United States Patent [19]

Zeleznick

[11] Patent Number: 5,260,021
[45] Date of Patent: Nov. 9, 1993

[54] HYDROGEN PEROXIDE-CONTAINING GELS AND CONTACT LENS DISINFECTING USING SAME

[75] Inventor: Lowell Zeleznick, Irvine, Calif.

[73] Assignee: Allergan, Inc., Irvine, Calif.

[21] Appl. No.: 905,630

[22] Filed: Jun. 29, 1992

[51] Int. Cl.⁵ .................. A01N 25/04; A61L 2/18
[52] U.S. Cl. .................. 422/28; 424/78.04; 514/839; 514/840; 514/944
[58] Field of Search .................. 424/78.04, 78.02; 514/839, 840, 944; 422/28; 252/174.23, 174.21, DIG. 14; 564/106

[56] References Cited

U.S. PATENT DOCUMENTS

| | | | |
|---|---|---|---|
| 3,657,413 | 4/1972 | Rosenthal | 424/78.02 X |
| 3,908,680 | 9/1975 | Krezanoski | 134/26 |
| 4,127,423 | 11/1978 | Rankin | 134/30 |
| 4,588,586 | 5/1986 | Kessler et al. | 424/94 |
| 4,826,658 | 5/1989 | Kay | 422/30 |
| 4,830,783 | 5/1989 | Ellis et al. | 252/174.23 X |
| 4,889,689 | 12/1989 | Tsao | 422/28 X |
| 4,921,630 | 5/1990 | Bhatia | 514/839 X |
| 5,008,106 | 4/1991 | Merianos et al. | 424/80 |

*Primary Examiner*—Robert J. Warden
*Assistant Examiner*—E. Leigh Dawson
*Attorney, Agent, or Firm*—Frank J. Uxa

[57] ABSTRACT

An antimicrobial composition in the form of a gel is effective to disinfect contact lenses. In one embodiment, the antimicrobial composition comprises: water; hydrogen peroxide in an amount effective to disinfect a contact lens contacted with the antimicrobial composition; and a gelling component in an amount effective to maintain the antimicrobial composition as a gel.

20 Claims, No Drawings

HYDROGEN PEROXIDE-CONTAINING GELS AND CONTACT LENS DISINFECTING USING SAME

BACKGROUND OF THE INVENTION

The present invention relates to compositions and methods useful for disinfecting contact lenses. More particularly, this invention relates to gelled antimicrobial compositions and to methods using such gelled antimicrobial compositions to disinfect contact lenses.

Contact lenses should be periodically disinfected by the user to prevent infection or other deleterious effects on ocular health which may be associated with contact lens wear. Currently, there are several different conventional systems and methods which enable the user to disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are oxidative disinfectant, in particular hydrogen peroxide, disinfection systems. Disinfecting hydrogen peroxide solutions are effective to kill the bacteria and fungi which may contaminate contact lenses. However, residual hydrogen peroxide on a disinfected contact lens may cause irritation, burning or other trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens.

There continues to be a need for a contact lens care system which effectively disinfects a contact lens and provides the user or wearer of the lens with assurance that the lens has been effectively disinfected and that the disinfected lens can be safely and comfortably worn.

SUMMARY OF THE INVENTION

New compositions and methods for disinfecting, and preferably cleaning, contact lenses have been discovered. The present system invites active user (contact lens wearer) involvement in the contact lens treatment methodology. In so doing, the lens wearer is given added assurance or confidence that the contact lens has been effectively treated and that the disinfectant has been effectively removed before the treated lens is placed in the eye. Moreover, no prolonged periods of waiting for the lens to be disinfected in a disinfectant-containing liquid solution are required. The contact lens is effectively treated while the user is actively involved. This positive or active involvement by the user reduces the problem of user compliance which often becomes apparent in other contact lens treatment methods which involve a series of steps spaced between prolonged waiting periods. The contact lens can be disinfected and cleaned in a single step. In effect, the user gets a comfortable feeling that he/she is in total control of treating his/her lens so that the lens is thoroughly treated.

In one broad aspect, the present invention involves antimicrobial compositions useful for disinfecting a contact lens. Such compositions comprise water; hydrogen peroxide in an amount effective to disinfect a contact lens contacted with the antimicrobial composition; and a gelling component in an amount effective to maintain the antimicrobial composition as a gel. The pH of the antimicrobial compositions is preferably in the range of about 5.5 to about 7.0.

In another broad aspect of the present invention, methods for disinfecting a contact lens comprise contacting the lens with an antimicrobial composition comprising water, hydrogen peroxide and a gelling component in an amount effective to maintain the composition as a gel prior to the contacting. This contacting occurs at conditions effective to disinfect the contact lens. Preferably, the contact lens wearer is actively involved in manually rubbing the composition on the lens to effect the disinfection.

DETAILED DESCRIPTION OF THE INVENTION

The present invention is of value with all types of contact lenses which are benefited by periodical disinfecting using hydrogen peroxide. Such contact lenses, e.g., conventional contact lenses, preferably soft contact lenses, may be made of any suitable material or combination of materials and may have any suitable configuration not substantially deleteriously affected by hydrogen peroxide.

The present antimicrobial compositions comprise water; hydrogen peroxide in an amount effective to disinfect contact lens disinfected with the antimicrobial composition; and a gelling component in an amount effective to maintain said antimicrobial composition as a gel.

The water portion of the present composition often comprises a major portion, that is at least about 50% by weight, of the total composition.

The antimicrobial compositions of the present invention include a contact lens disinfecting amount of hydrogen peroxide. Preferably, a contact lens disinfecting amount of hydrogen peroxide means such amount as will reduce the microbial burden by one log order in three hours. Still more preferably, the hydrogen peroxide concentration is such that the antimicrobial load is reduced by one log order in one hour. Particularly preferred are those hydrogen peroxide concentrations which reduce the microbial load by one log order in ten minutes or less. The present antimicrobial compositions preferably contain about 0.5% or about 1.5% to about 6% (w/v) of hydrogen peroxide. These compositions are effective at killing bacteria and fungi which may be found on contact lenses.

The gelling component is present in an amount effective to maintain the antimicrobial composition as a gel. As used herein, the term "gel" refers to a jellylike or gelatinous material in which the aqueous phase is entrapped or immobilized and is not free. Such gels are formed by combining a sufficient amount of gelling component with water and one or more other components, such as the other component or components of the present system, at conditions effective to produce the desired gel. The present gels are substantially different from the water-like, hydrogen peroxide-containing aqueous solutions conventionally used to disinfect contact lenses.

The gelling component is preferably present in an amount in the range of about 0.5% to about 20% (w/v) of the antimicrobial composition.

Any suitable gelling component may be used in the present compositions, provided that such gelling component functions as described herein and has no substantial detrimental effect on the contact lens being treated, on the contact lens treating method, or on the wearer of the contact lens. Examples of useful gelling components include carboxypolymethylene, for example, such materials sold by B.F. Goodrich under the trademark Carbopol, polyethylene-polypropyleneglycols, for example, such materials sold by BASF under the trademark Poloxamer, and the like and mixtures thereof.

The present antimicrobial compositions preferably include a wetting component, for example, one or more surfactants such as those conventionally employed in contact lens care products, in an amount effective to facilitate the contacting of the antimicrobial composition and the contact lens.

One or more additional component or components may be included in the present compositions to impart or provide at least one beneficial or desired property to the compositions. Such additional components may be selected from components which are conventionally used in one or more contact lens care, e.g., disinfecting and/or cleaning, compositions. Examples of such additional components include buffering agents, cleaning agents, nutrient agents, sequestering agents, tonicity agents, contact lens conditioning agents, and the like. These additional components may each be included in the present compositions in an amount effective to impart or provide the beneficial or desired property. For example, such additional component or components may be included in the present compositions in amounts similar to the amounts of such components used in other, e.g., conventional, contact lens care compositions.

Useful buffering agents include, but not limited to, acetate buffers, citrate buffers, phosphate buffers, carbonate buffers, bicarbonate buffers and borate buffers.

Useful sequestering agents include, but are not limited to, disodium ethylene diamine tetraacetate, alkali metal hexametaphosphate, citric acid, sodium citrate and mixtures thereof.

Useful tonicity adjustors include, but are not limited to, sodium chloride, potassium chloride, mannitol, dextrose, glycerin, propylene glycol and mixtures thereof.

In a particularly useful embodiment, the present gelled antimicrobial compositions further include at least one enzyme effective to remove debris from a contact lens. Among the types of debris that form on a contact lens during normal use are protein-based debris, mucin-based debris, lipid-based debris and carbohydrate-based debris. One or more types of debris may be present on a single contact lens.

The enzyme employed may be selected from enzymes which are conventionally employed in the enzymatic cleaning of contact lenses. For example, many of the enzymes disclosed in Huth et al U.S. Pat. No. Re. 32,672 and Karageozian et al U.S. Pat. No. 3,910,296 are useful in the present invention. Each of these patents is incorporated in its entirety by reference herein. Among the useful enzymes are those selected from proteolytic enzymes, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus, II Alkaline Proteases", Biotechnology and Bioengineering, Vol. XII, pp 213-249 (1970) and Keay, L. and Moser, P. W., "Differentiation of Alkaline Proteases form Bacillus Species" Biochemical and Biophysical Research Comm., Vol 34, No. 5, pp 600-604, (1969).

The subtilisin enzymes are broken down into two sub-classes, subtilisin A and subtilisin B. In the subtilisin A grouping are enzymes derived from such species as *B. subtilis, B. licheniformis* and *B. pumilis.* Organisms in this sub-class produce little or no neutral protease or amylase. The subtilisin B sub-class is made up of enzymes from such organisms as *B. subtilis, B. subtilis var. amylosaccchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *B. polymyxa*).

An effective amount of enzyme is to be used in the practice of this invention. Such amount will be that amount which effects removal in a reasonable time of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the excipient it contains.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent. Thus, for any given enzyme, there is a particular pH range in which that enzyme will function best. The determination of such range can readily be done by known techniques.

The present antimicrobial compositions may be prepared, for example, using techniques conventionally employed to make aqueous gels. For example, the components of the composition may be combined and mixed together sufficiently to form a substantially uniform gel. In one useful embodiment all the water soluble components of the composition are first combined with and dissolved in the water portion which is then combined and mixed with the gelling component to produce the desired gel. It may be desirable to allow the combined components to remain undisturbed for a period of time so that the gel can be formed.

An acidic component and/or a basic component may be included during the preparation of the present antimicrobial compositions to provide the antimicrobial compositions with the desired pH.

For example, if it is desired to raise the pH of the gel, an amine, such as an alkanolamine, for example, triethanolamine, may be included. On the other hand, if it is desired to lower the pH of the gel, an acid, such as phosphoric acid, hydrochloric acid and the like, may be included.

During the disinfecting contacting, it is preferred that the antimicrobial composition have a pH of less than about 8, more preferably in the range of about 5.5 to about 7.0 or about 7.5.

The disinfecting contacting preferably includes manually rubbing the antimicrobial composition on the contact lens being disinfected and cleaned. This manual rubbing, which preferably is conducted for a period of time in the range of about 30 seconds to about 3 or about 5 or about 10 minutes, is very effective to actively involve the wearer of the contact lens in the disinfecting/cleaning of the contact lens. This active involvement gives the contact lens wearer added assurance and confidence that his/her contact lens is being properly treated.

After such contacting, the contact lens may be contacted with a liquid aqueous medium, for example, a saline solution, in an amount effective to remove all the antimicrobial composition from the lens. For example, the disinfected contact lens can be rinsed free of such antimicrobial composition with a conventional saline solution.

As an added assurance that the treated contact lens includes no residual antimicrobial composition, the present antimicrobial compositions preferably include a dye component in an amount effective to give the composition a distinctive color. Thus, as the antimicrobial composition is removed from the disinfected contact lens, the distinctive color of the composition is also removed from the lens. The complete absence of this distinctive color from the contact lens signals the lens user that the contact lens is ready for insertion into the eye for safe and comfortable wear.

In one embodiment, the disinfected contact lens is contacted, e.g., rinsed, with an aqueous liquid medium containing a hydrogen peroxide destroying component (HPDC) in an amount effective to destroy all the residual hydrogen peroxide present on the contact lens.

Any suitable HPDC may be employed provided such HPDC has no substantial detrimental effect on the present system, on the disinfected lens or on the wearer of the disinfected lens. Among the useful HPDC are hydrogen peroxide reducing agents, peroxidases (meaning to include therein catalase) and mixtures thereof.

Examples of hydrogen peroxide reducing agents which are useful in the present invention are alkali metal in particular sodium, thiosulfates; thiourea; alkali metal, in particular sodium, sulfites; thioglycerol; alkali metal, in particular sodium, formates; pyruvic acid and salts of pyruvic acid; N-acetylcysteine; ene-diol compounds, e.g., ascorbic acid compounds, reductive acid compounds, isoascorbic acid compounds, glyoxylic acid compounds, squaric acid compounds, dihydroxymaleic acid compounds, dihydroxyfumaric acid compounds, and mixtures thereof. Typical examples of the foregoing ene-diol compounds are the acids themselves, e.g., ascorbic acid, ophthalmically acceptable salts of such acids, e.g., sodium ascorbate, ophthalmically acceptable esters of such acids, e.g., ascorbyl palmitate and any other ophthalmically acceptable derivatives of such acids, e.g., that retain the ene-diol molecular structure, mixtures thereof and the like.

A particularly useful peroxidase is catalase. The peroxidases, and especially catalase, are very beneficial in the present invention since such HPDCs are effective to substantially eliminate hydrogen peroxide from a liquid medium in a reasonable period of time, e.g., on the order of about 1 minute to about 12 hours, preferably about 5 minutes to about 1 hour, after the HPDC is initially released into the liquid medium.

The amount of HPDC employed is preferably sufficient to destroy all the hydrogen peroxide present in the liquid medium into which the HPDC is placed. Excess HPDC may be employed. Very large excesses of HPDC are to be avoided since the HPDC itself may cause problems with the disinfected lens and/or the ability to safely and comfortably wear such disinfected lens. When catalase is employed as an HPDC, it is preferably present in an amount of about 100 to about 1000, more preferably about 150 to about 700, units of catalase activity per milliliter of liquid medium.

If a peroxidase is used as an HPDC, it is preferred that the lens be contacted, e.g., rinsed, with a further aqueous liquid medium, such as a conventional saline solution, to remove the residual peroxidase before placing the contact lens in the eye for wear.

The following, non-limiting examples illustrate certain aspects of the present invention.

EXAMPLE 1

An aqueous medium is prepared by combining together 3.0% (w/v) hydrogen peroxide, 3% (w/v) carboxypolymethylene and triethanolamine with the remainder of the composition being liquid water. The triethanolamine is included to provide a final gelled composition having a pH of 6.5. The various components noted above are combined and mixed together to form a gelled composition.

A quantity of this gelled composition is placed on the forefinger of a contact lens wearer. A contact lens is placed on top of this gel composition and the contact lens wearer proceeds to rub the contact lens between his forefinger and thumb, thereby effecting intimate contact between the gelled composition and the contact lens. This rubbing continues to approximately two minutes. At the end of this time, the contact lens is subjected to rinsing with a saline solution containing an effective amount of catalase to destroy all the hydrogen peroxide present on the contact lens. The rinsed contact lens, which is found to be effectively disinfected, is further rinsed with a conventional saline solution and is then placed in the eye for safe and comfortable wear without eye irritation.

EXAMPLE 2

Example 1 is repeated except that the gelled composition includes about 0.012 Anson Units of Subtilisin A enzyme.

The contact lens after being contacted with the gelled composition is rinsed with a catalase-containing saline solution, as described in Example 1, and is found to be disinfected and effectively free of proteinaceous deposit material. The contact lens is further rinsed with a conventional saline solution and is then placed in the eye for safe and comfortable wear without eye irritation.

EXAMPLE 3

A gelled composition as set forth in Example 1 is prepared except that the composition further includes a conventional, ophthalmically acceptable dye component which provides the gelled composition with a distinctive blue color.

This gelled composition is contacted with a contact lens substantially as set forth in Example 1. After this contacting, the contact lens is rinsed with a conventional saline solution until the distinctive blue color of the gelled composition is no longer present on the contact lens. At this point, the contact lens, which is found to be effectively disinfected, is placed in the eye for safe and comfortable wear, without eye irritation.

EXAMPLE 4

Example 3 is repeated except that the gelled composition includes about 0.012 Anson Units of Subtilisin A enzyme.

The rinsed contact lens, which is found to be effectively disinfected and free of proteinaceous deposit material, is placed in the eye for safe and comfortable wear without eye irritation.

While this invention has been described with respect to various specific examples and embodiments, it is to be understood that the invention is not limited thereto and that it can be variously practiced within the scope of the following claims.

What is claimed is:

1. An antimicrobial composition useful for disinfecting a contact lens comprising:
   water in an amount of at least about 50% by weight of an antimicrobial composition;
   hydrogen peroxide in an amount effective to disinfect a contact lens contacted with said antimicrobial composition; and
   a gelling component in an amount effective to maintain said antimicrobial composition as a gel.

2. The antimicrobial composition of claim 1 which has a pH in the range of about 5.5 to about 7.0.

3. The antimicrobial composition of claim 1 wherein said hydrogen peroxide is present in an amount in the range of about 1.5% to about 6% (w/v) of said antimicrobial composition.

4. The antimicrobial composition of claim 1 which further comprises a wetting component in an amount effective to facilitate the contacting of said antimicrobial composition and the contact lens.

5. The antimicrobial composition of claim 1 which further comprises a dye component in an amount effective to give said antimicrobial composition a distinctive color.

6. The antimicrobial composition of claim 1 which further comprises at least one enzyme capable of removing debris from a contact lens in an amount effective to remove debris from a debris laden contact lens.

7. The antimicrobial composition of claim 1 wherein said gelling component is present in an amount in the range of 0.5% to about 20% (w/v) of said antimicrobial composition.

8. The antimicrobial composition of claim 1 wherein said gelling component is selected from the group consisting of carboxypolymethylene, polyethylene-polypropyleneglycols and mixtures thereof.

9. A method for disinfecting a contact lens which comprises:
   contacting a contact lens with an antimicrobial composition comprising water in an amount of at least about 50% by weight of said antimicrobial composition, hydrogen peroxide in an amount effective to disinfect said contact lens and a gelling component in an amount effective to maintain said antimicrobial composition as a gel prior to said contacting, said contacting occurring at conditions effective to disinfect said contact lens.

10. The method of claim 9 wherein said contacting step comprises manually rubbing said antimicrobial composition on said contact lens.

11. The method of claim 9 wherein said antimicrobial composition has a pH in the range of about 5.5 to about 7.0 during said contacting.

12. The method of claim 9 wherein said contact lens is further contacted with an aqueous liquid medium to remove said antimicrobial composition from said contact lens.

13. The method of claim 12 wherein said aqueous liquid medium includes a hydrogen peroxide destroying component in an amount effective to destroy or cause the destruction of substantially all the hydrogen peroxide on said contact lens.

14. The method of claim 9 wherein said hydrogen peroxide is present in an amount in the range of about 1.5% to about 6% (w/v) of said antimicrobial composition.

15. The method of claim 9 wherein said antimicrobial composition further comprises a wetting component in an amount effective to facilitate said contacting.

16. The method of claim 9 wherein said antimicrobial composition further comprises a dye component in an amount effective to give said antimicrobial composition a distinctive color.

17. The method of claim 9 wherein said antimicrobial composition further comprises at least one enzyme capable of removing debris from a debris laden contact lens, and said contacting is effective to remove debris from said contact lens.

18. The method of claim 9 wherein said gelling component is present in an amount in the range of 0.5% to about 20% (w/v) of said antimicrobial composition.

19. The method of claim 9 wherein said gelling component is selected from the group consisting of carboxypolymethylene, polyethylenepolypropyleneglycols and mixtures thereof.

20. A method for disinfecting a contact lens which comprises:
   manually rubbing a contact lens with an antimicrobial composition comprising water, hydrogen peroxide in an amount effective to disinfect said contact lens and a gelling component in an amount effective to maintain said antimicrobial composition as a gel prior to said manual rubbing, thereby disinfecting said contact lens; and, thereafter,
   contacting said contact lens with an aqueous medium to remove said antimicrobial composition from said contact lens.

* * * * *